(12) United States Patent
Kim et al.

(10) Patent No.: US 8,624,039 B2
(45) Date of Patent: Jan. 7, 2014

(54) METHOD FOR PREPARING [$^{18}$F]FALLYPRIDE WITH LOW BASE CONCENTRATION

(75) Inventors: Sang Eun Kim, Seoul (KR); Byung Chul Lee, Seoul (KR); Byung Seok Moon, Seoul (KR); Yu Kyeong Kim, Seoul (KR)

(73) Assignee: SNU R&DB Foundation, Seoul (KR)

( * ) Notice: Subject to any disclaimer, the term of this patent is extended or adjusted under 35 U.S.C. 154(b) by 36 days.

(21) Appl. No.: 13/395,841

(22) PCT Filed: Mar. 4, 2010

(86) PCT No.: PCT/KR2010/001351
§ 371 (c)(1),
(2), (4) Date: Mar. 13, 2012

(87) PCT Pub. No.: WO2011/030981
PCT Pub. Date: Mar. 17, 2011

(65) Prior Publication Data
US 2012/0178920 A1   Jul. 12, 2012

(30) Foreign Application Priority Data
Sep. 14, 2009  (KR) .................. 10-2009-0086354

(51) Int. Cl.
*C07D 207/09* (2006.01)
(52) U.S. Cl.
USPC ........................................................ 548/567
(58) Field of Classification Search
None
See application file for complete search history.

(56) References Cited

FOREIGN PATENT DOCUMENTS

| CN | 101157648 A | 4/2008 |
|---|---|---|
| CN | 101157649 A | 4/2008 |
| WO | WO 2004/089517 A1 | 10/2004 |

OTHER PUBLICATIONS

Mukherjee et al. "Fluorinated Benzamide Neuroleptics-III. Development of (S)-N-[(1-allyl-2-pyrrolidinyl)methyl]-5-(3-[$^{18}$F]fluoropropyl)-2,3-dimethoxybenzamide as an Improved Dopamine D-2 Recetpor Tracer," *Nucl. Med. Biol.*, 22(3):283-296 (1995).
Lu et al. "Synthesis of [$^{18}$F] Fallypride in a Micro-Reactor: Rapid Optimization and Multiple-Production in Small Doses for Micro-PET Studies," *Current Radiopharmaceuticals*, 2(1):49-55 (2009).
International Search Report from parent PCT/KR2010/001351 (Nov. 1, 2010).
Herraiz and Casal "Evaluation of solid-phase extraction procedures in peptide analysis," *J. Chrom. A*, 708:209-221 (1995).
Donohue et al. "Discovery and Labeling of High-Affinity 3,4-Diarylpyrazolines as Candidate Radioligands for In Vivo Imaging of Cannabinoid Subtype-1 ($CB_1$) Receptors," *J. Med. Chem.*, 51:5608-5616 (2008).

*Primary Examiner* — Michael Barker
(74) *Attorney, Agent, or Firm* — Klarquist Sparkman, LLP (57) ABSTRACT

A method for preparing [$^{18}$F]fallypride is disclosed, which comprises a first step for trapping a fluorine-18 to a polymer ion exchange cartridge; a second step for extraction of fluorine-18 by inputting low base concentrations: 5.0~25 μL of 40% $TBAHCO_3$ or K2.2.2./$K_2CO_3$ (5~25 mg/0.5~3.0 mg) as a phase-transfer catalyst in a mixture of alcohol/water (1.0/0.2 (v/v)) or alcohol as a solvent into the polymer ion exchange cartridge trapped by the fluorine-18; a third step for preparing a [$^{18}$F]fallypride product by removing the solvent from the trapped fluorine-18, by inputting tosylate precursor in $CH_3CN$ as a solvent into a reactor and by reacting the same for 5~35 minutes at 50~120° C.; and a fourth step for preparing a pure [$^{18}$F]fallypride by purifying the prepared [$^{18}$F]fallypride product.

6 Claims, 5 Drawing Sheets

METHOD FOR PREPARING [$^{18}$F]FALLYPRIDE WITH LOW BASE CONCENTRATION

CROSS REFERENCE TO RELATED APPLICATIONS

This is the U.S. National Stage of International Application No. PCT/KR2010/001351, filed Mar. 4, 2010, which was published in English under PCT Article 21(2), which in turn claims the benefit of Korean Patent Application No. 10-2009-0086354, filed Sep. 14, 2009.

TECHNICAL FIELD

The present invention relates to a method for preparing [$^{18}$F]fallypride with low base concentration.

BACKGROUND ART

It is known that the receptor located in a neural cell membrane in a synapse stimulates nerve signals transmitted through G-protein linked receptors and ligand-gated ion channels with the help of neurotransmitter such as dopamine and serotonin. Part of a neurotransmitter receptor is located in a presynaptic nerve cell membrane for reuptaking neurotransmitter or is located in a cell body for a negative feedback function. The targets to be coupled by a radiotracer generally used for evaluating the imagined transmission system might be the whole processes related with the creation, movement and decomposition of neurotransmitter. It is possible to image and quantify the functions of cranial nerves and the changes due to diseases by using enzyme involved in a synthesis of neurotransmitter, a post synaptic receptor isolated and coupled in a form of synapse, a transporter which reuptakes a neurotransmitter isolated in synapse through a presynaptic nerve terminal, and a radiotracer which is selectively coupled to enzyme which decomposes a neurotransmitter.

The radiotracer used for the image of a neurotransmitter receptor must have a high binding affinity and selectivity and must have less non-specific binding in tissues which does not have any receptor. In addition, it is required that the radiotracer must fast pass through a blood brain barrier, generating less metabolite after being administrated into blood, and the produced metabolite must be fast eliminated from the blood in order to prevent being reabsorbed into brain.

The radiotracer currently used in a clinic or aresearch can be classified into a SPECT for a radiotracer and a PET for a radiotracer depending on the kinds of labeled isotope. The tracer with radioisotopes such as $^{123}$I ($t_{1/2}$=13 h) or $^{99m}$Tc ($t_{1/2}$=6 h), which has a relatively longer half life, for thereby obtaining a SPECT image. The SPECT disadvantageously has a poor accuracy in a resolution and quantification of the image as compared to the PET. Therefore, radiotracers are currently focused on the development of PET radiotracers which have PET isotope like $^{11}$C ($t_{1/2}$=20 min) and $^{18}$F ($t_{1/2}$=110 min).

The dopamine receptor antagonist [$^{18}$F]fallypride, {(S)-N-[(1-allyl-2-pyrrolidinyl)methyl]-5-(3-[$^{18}$F]-fluoropropyl)-2,3-dimethoxybenzamide}, which has the extremely selectivity and high affinity for $D_2$ and $D_3$ subtype and poor affinity for the $D_4$ subtype, is currently being used as a potential dopamine $D_2/D_3$ receptor imaging agent by positron emission tomography (PET).

As the cortical dopamine function related with cognition in neuropsychiatric illness has been more importantly considered, [$^{18}$F]fallypride has caught more attention with its capability of visualization of extrastriatal $D_2$ receptors as well as striatal $D_2$ receptors. In addition, the relatively longer half-life of radionuclide (fluorine-18, $t_{1/2}$=110 min) in [$^{18}$F]fallypride provides good prospects in assessing low concentration of extrastriatal dopamine $D_2/D_3$ receptors. Therefore, the efficient radiochemical synthesis of [$^{18}$F]fallypride is important with the high radiochemical yield and specific activity for routine clinical research studies. As seen in the following reaction formula 1, the synthesis of [$^{18}$F]fallypride can be conducted by labeling of fluorine-18 with tosyl-fallypride (tosylate precursor) (2) using phase-transfer catalyst.

[Reaction formula 1]

[$^{18}$F]Fallypride

In the preparation of [$^{18}$F]fallypride, Mukgerjee and coworkers reported the moderate yields about 20-40% with 33-63 GBq/mol of specific activity and relatively long incorporation time of fluorine-18 with tosyl-fallypride about 30 min in manual synthesis. Moreover, the lengthy purification process of HPLC had to follow to avoid mass peaks due to significant thermal degradation of the precursor, the formation of the corresponding alcohol, or olefin resulting from elimination reactions, as well as other unidentified peaks in approximately 2 mg of precursor scales. In some cases, further purification of [$^{18}$F]fallypride appears to be necessary in order to obtain higher specific activities.

The method for automatically synthesizing [$^{18}$F]fallypride was proposed, which uses a RDS-112 CPCU (CTI) or TracerLab FX-FN (GE Healthcare). Although it has been shown using automated synthesis that [$^{18}$F]fallypride can be prepared by one-step radiochemical synthesis with a tosylate precursor, the radiochemical yields are somewhat low (5-20%), for the same reason described above in manual synthesis. (Ansari et al., 2006. Comparison of three [$^{18}$F] fallypride methods intended for automated remote chemistry modules. J. Nucl. Med. 47 (suppl), 159S Shiet al., 2002. Automated clinical production of F-18 radiopharmaceuticals with electrophilic or nucleophilic substitution in a custom manufactured fluorination module. J. Nucl. Med. 43 (suppl.), 1522S) Recently, microfluidic devices with milder reaction conditions have emerged to produce radiotracers for molecular imaging by microPET (Gillies et al., 2005. Microfluidic reactor for the radiosynthesis of PET radiotracers. Appl. Radiat. Isot. 64 (3), 325-332 Jeffery et al., 2004. Radiochemistry on microfabricated devices: Proof of principle. J. Nucl. Med. 45 (Suppl. 2), 51P Lee et al., 2005. Multistep synthesis of a radiolabeled imaging probe using integrated microfluidics. Science 310 (5755), 1793-1796 Liow et al., 2005. Preliminary studies of conducting high level production radiosynthesis using microfluidic devices. J. Label. Compd. Radiopharm. 48, (Suppl.), S28 Lu et al., 2009 Synthesis of [$^{18}$F]fallypride in a micro-reactor: Rapid optimization and multiple-production in small doses for microPET studies. Curr. Radiopharm. 2 (1), 49-55 Lucignani, G., 2006. Pivotal role of nanotechnologies and biotechnologies for molecular imaging and therapy. Eur. J. Nucl. Med. Mol. Imaging. 33 (7), 849-851 Steel et al., 2007. Automated PET radiosyntheses using microfluidic devices. J. Label. Compd. Radiopharm. 50 (5), 308-311). It has several advantages including the use of lower amounts of precursor and base, easier and more efficient purification, relatively high conversion yield, and short preparation time. The successful production of [$^{18}$F]fallypride with micro-reaction devices in small doses of about 0.5-1.5 mCi was reported (Lu et al., 2009 Synthesis of [$^{18}$F]fallypride in a micro-reactor: Rapid optimization and multiple-production in small doses for microPET studies. Curr. Radiopharm. 2 (1), 49-55), although high-dose-scale production was not addressed. More recently, some groups have reported moderate radiochemical yields in automated [$^{18}$F]fallypride production of about 20-40% (Ansari et al., 2006. Comparison of three [$^{18}$F]fallypride methods intended for automated remote chemistry modules. J. Nucl. Med. 47 (suppl), 159S Kuhnast et al., 2009. Production of [$^{18}$F]fallypride on a tracerlab FX-FN synthesizer. J. Label. Compd. Radiopharm. 52 (suppl.), 286S Lukic et al., 2009. Fully automated system for [$^{18}$F]fallypride routine production with tracerlab MX module. J. Label. Compd. Radiopharm. 52 (suppl.), 315S Mock et al., 2009. Fully automated synthesis of [$^{11}$C]fallypride and [$^{18}$F]fallypride. J. Label. Compd. Radiopharm. 52 (suppl.), 258S Vuong et al., 2009. [$^{18}$F]fallypride synthesis with protic solvent mixture. J. Label. Compd. Radiopharm. 52 (suppl.), 298S). In these studies, however, production proceeded at high temperatures (150-165° C.) or involved the use of an unusual microwave system in automatic devices. Moreover, various by-products were produced during HPLC purification as described above. The use of high base concentrations in the fluorine-18 labeling step is likely the main reason why various side products were generated, providing low radiochemical yield particularly in the case of base-sensitive tosyl-fallypride.

In automatic synthesis, QMA or Chromafix PS-HCO$_3$ cartridge was frequently used in capture-release manner to extract fluorine-18 ion because fluorine-18 is produced in largely diluted $^{18}$O-enriched water. In that time, fluorine-18 could be released from polymer cartridge by elution with relatively large amounts of K$_2$CO$_3$/K2.2.2., CsCO$_3$/K2.2.2., TBAOH, or TBAHCO$_3$ etc. Such large amounts of base (>3 mg for K$_2$CO$_3$>30 µL for TBAHCO$_3$) lead to more than the expected amounts of various side products, and hence require more quantity of precursor and diminish radiochemical yield and purity. Thus, the incorporation of fluorine-18 into base-sensitive [$^{18}$F]fallypride has not been achieved in high radiochemical yields until now because fluorine-18 could not elute from ion exchange cartridge over 95% in relatively low base concentration (small amounts of phase-transfer catalyst).

For routine clinical use of [$^{18}$F]fallypride, an automated preparation with a high radiochemical yield and purity are required.

The inventors of the present application demonstrated the minimization of base concentration when fluorine-18 was eluted from the ion exchange cartridge in radiosynthesis using the utility of a commercial TracerLab FX$_{FN}$ chemistry module and also described the production of [$^{18}$F]fallypride in relatively high-doses with high specific activity, purity and shortened preparation time for routine clinical use, which resulted in the present invention.

DISCLOSURE OF INVENTION

Technical Problem

For routine clinical use of [$^{18}$F]fallypride, an automated preparation with a high radiochemical yield and purity are required.

Solution to Problem

The inventors of the present application demonstrated the minimization of base concentration when fluorine-18 was eluted from the ion exchange cartridge in radiosynthesis using the utility of a commercial TracerLab FX$_{FN}$ chemistry module and also described the production of [$^{18}$F]fallypride in relatively high-doses with high specific activity, purity and shortened preparation time for routine clinical use, which resulted in the present invention.

Advantageous Effects of Invention

In the method for preparing [$^{18}$F]fallypride according to the present invention, it is possible to improve the radiochemical yield and purity of [$^{18}$F]fallypride with low base concentration method except high temperature (150-165° C.) or microwave system. The present invention also can be well applied to a labeling of other base sensitive precursors in order to highly efficient automatic production.

BRIEF DESCRIPTION OF DRAWINGS

The present invention will become better understood with reference to the accompanying drawings which are given only by way of illustration and thus are not limitative of the present invention, wherein.

MODE FOR THE INVENTION

The method for preparing [$^{18}$F]fallypride according to the present invention comprises: trapping a fluorine-18 to a polymer ion exchange cartridge; eluting (extraction) a fluorine-18 by inputting 5.0~30 µL of 40% TBAHCO$_3$ or K2.2.2./K$_2$CO$_3$ (5~25 mg/0.5~3.0 mg) as a phase-transfer catalyst in a mixture solution of alcohol/water (1.0 mL/0.2 mL (v/v)) or alcohol (1.2 mL) as eluting solvent into the polymer ion exchange cartridge trapped by the fluorine-18; preparing a [$^{18}$F]fallypride product by removing the solvent from the extracted fluorine-18, by inputting tosylate precursor in $CH_3CN$ as a reaction solvent into a reactor and by reacting for 5~35 minutes at 50~120° C.; and separating a pure [$^{18}$F]fallypride by high performance liquid chromatography.

In the first step, a fluorine-18 is trapped on an ion exchange cartridge.

In this step, the fluorine-18 can be trapped by passing O-18 water ($H_2^{18}O$) containing fluorine-18 through a polymer ion exchange cartridge in a known method.

At this time, the polymer ion exchange cartridge might consist of QMA cartridge or a Chromafix PS-$HCO_3$ cartridge, but is not limited thereto.

In the second step, fluorine-18 is eluted by introducing a phase-transfer catalyst into the polymer ion exchange cartridge trapped with the fluorine-18 in the first step.

The fluorine-18 trapped on the polymer ion exchange cartridge might be extracted from the polymer cartridge by means of the phase-transfer catalyst (base) elution. At this time, the phase-transfer catalyst is preferably minimized because various impurities with side products might be produced in the course of reacting between tosylate-precursor and fluorine-18.

In the method for preparing [$^{18}$F]fallypride according to the present invention, the phase-transfer catalyst can use 40% $TBAHCO_3$ or K2.2.2./$K_2CO_3$.

In event that 40% $TBAHCO_3$ is used as a phase-transfer catalyst, the amount of use is preferably is 5.0~25 L. In event that the amount of use of 40% $TBAHCO_3$ is less than 5.0 μl, F-18 does not well extract from the cartridge. When it exceeds 30 μL, the fluorine-18 labeling reaction becomes poor.

In event that K2.2.2./$K_2CO_3$ is used as the phase-transfer catalyst, the amount of its use is generally not limited with respect to K2.2.2, but 5~25 mg is generally used. In this case, the amount of $K_2CO_3$ is preferably 0.5~3.0 mg. In event that the amount of use of $K_2CO_3$ is less than 0.5 mg, F-18 does not well extract from the cartridge. When it exceeds 3.0 mg, the fluorine-18 labeling also becomes poor.

In the method for preparing [$^{18}$F]fallypride according to the present invention. It is preferred that the solvent used for extracting the phase-transfer catalyst is a mixture of alcohol and water or is alcohol. Here, the alcohol can have a straight-chained or branch-chained alkyl group having from 1 to 6 carbon atoms, such as methanol, ethanol, propanol, isopropanol, n-butanol, t-butanol, t-amylalcohol, 2,3-dimethylbutane-2-ol, but is not limited thereto.

The volume ratio (v/v) of alcohol and water is preferably 1.0:0.2. In event that the ratio is out of the above range of ratio, it only takes a lot of time in removing the extraction solvent, therefore it not limited thereto.

In the method for preparing [$^{18}$F]fallypride according to the present invention, the extraction (recovery) ratio of fluorine-18 was measured while changing the kinds and amount of phase-transfer catalyst. Fluorine-18 trapped into the Chromafix PS-$HCO_3$ cartridge was eluted by various base concentrations, solvents, and phase-transfer catalysts, resulting in rates of recovery ranging from 18% to over 95% as summarized in Table 1. The extracted fluorine-18 was obtained over 95% from the PS-$HCO_3$ cartridge in entry 3, 5, 8, and 10 [Table 1; K2.2.2./$K_2CO_3$ (13/3 mg) in $CH_3CN/H_2O$ (entry 3), K2.2.2./$K_2CO_3$ (11/0.8 mg) in MeOH/$H_2O$ (entry 5), $TBAHCO_3$ (30 μL) in $CH_3CN/H_2O$ (entry 8) and $TBAHCO_3$ (10 μL) in MeOH/$H_2O$ (entry 10)]. The fully automated synthesis of [$^{18}$F]fallypride, therefore, was performed in these fluorine-18 eluting conditions in which over 95% of the radioactivity was extracted from the cartridge. Other conditions (entries 1, 2, 4, 6, 7, and 9) with lower base concentrations do not meet clinical production standards even with high radiolabeling yield and low side product levels due to the high loss of radioactivity separated from the ion exchange cartridge.

As a result of the above measurement, it was known that 40% $TBAHCO_3$ (10 μL) or K2.2.2./$K_2CO_3$ (11/0.8 mg) could be preferably used as a phase-transfer catalyst among four conditions when preparing [$^{18}$F]fallypride, and MeOH/$H_2O$ (1.0/0.2 (v/v)) or MeOH could be preferably used as an elution solvent. Because when MeOH/$H_2O$ solution was used, trapped F-18 could be extracted by more small amounts of base (phase-transfer catalyst) over 95% from ion cartridge.

In the third step, the solvent of fluorine-18 eluted in the second step was removed, and tosylate precursor in $CH_3CN$ as reaction solvent were inputted into a reactor and were reacted each other for thereby preparing [$^{18}$F]fallypride production.

In the present invention, the use of K2.2.2./$K_2CO_3$ (13/3.0 mg, entry 1, Table 2) at 100° C. for 30 min led to a lower radiochemical yield of about 26%. In addition, HPLC purification revealed olefin or unidentified peaks and there are overlapped with [$^{18}$F]fallypride. The use of 40% $TBAHCO_3$ (30 μL, entry 3, Table 2) under the same conditions also led to a relatively low radiochemical yield of about 44%. However, readiopeaks were completely separated with no overlapping organic impurities despite isocratic HPLC conditions. The optimal conditions for [$^{18}$F]fallypride production were K2.2.2./$K_2CO_3$ (11/0.8 mg, entry 2) and 10 μL of 40% $TBAHCO_3$ (entry 4), each of which gave a 71% radiochemical yield and required a total preparation time of about 74 min. However, HPLC purification revealed slightly more impurities in the K2.2.2./$K_2CO_3$ (10.8 mg, entry 2) condition than in the 40% $TBAHCO_3$ condition (entry 4).

In addition, shortening the labeling time from 30 to 10 min in the 40% $TBAHCO_3$ (10 μL) condition still gave a high radiochemical yield of 68% within a total elapsed time of 51 min (entry 5), with a high specific activity of about 140-192 GBq/μmol. Though the result of entry 4 showed a slightly higher radiochemical yield than that of entry 5 with taking decay-corrected factor, both automatic synthesis conditions showed similar radiochemical yields of about 46-50% without decay-correction. Consequently, Since [$^{18}$F]fallypride was a radioactive substance having a certain half life, the radioactivity decreased as time passes. Shortening the incorporation time of fluorine-18 (10 min, entry 5) is useful in considering practical clinical use. This was mainly due to the fact that 10 min was sufficient for labeling at the optimal temperature without another driving force such as high temperature (165° C.) and microwave.

In the fourth step, a pure [$^{18}$F]fallypride obtained by purifying [$^{18}$F]fallypride prepared in the third step.

In the fourth step, a conventional purification method was used. For example, the HPLC method was used in order to purify [$^{18}$F]fallypride for thereby preparing a pure [$^{18}$F]fallypride.

[$^{18}$F]Fallypride which was prepared by the above method had a radiochemical yield of 70% after decay correction and had a radiochemical purity of above 97% with a high specific activity of 140-192 GBq/μmol. The total preparation time was about 50 minutes, which were shorter than the reported methods.

In the method for preparing [$^{18}$F]fallypride according to the present invention by adjusting (briefly, minimizing) the kinds and concentration of base when fluorine-18 was isolated from the ion exchange cartridge, it was possible to enhance the radiochemical yield of [$^{18}$F]fallypride (about 70%) as compared to reported methods. In addition, it was possible to shorten the preparation time about 20 minutes. Consequently, [$^{18}$F]fallypride prepared by present invention can be obtained with a higher purity and a higher yield for a shorter time thereby being well applied to a clinical research studies by positron emission tomography (PET).

The above preparation method can be well applied to a preparation of [$^{18}$F]fallypride and this method will be applied to FP-CIT (N-2-Fluoropropyl-3-β-(4-iodophenyl)nortropane-2-β-carboxylic acid), FAZA (1-(5-Deoxy-5-fluoro-α-D-arabinofuranosyl)-2-nitroimidazole), and FDDNP (2-(1,1-Dicyanopropen-2-yl)-6-(fluoroethyl)methylamino) naphthalene) which are base-sensitive.

Figure 4:
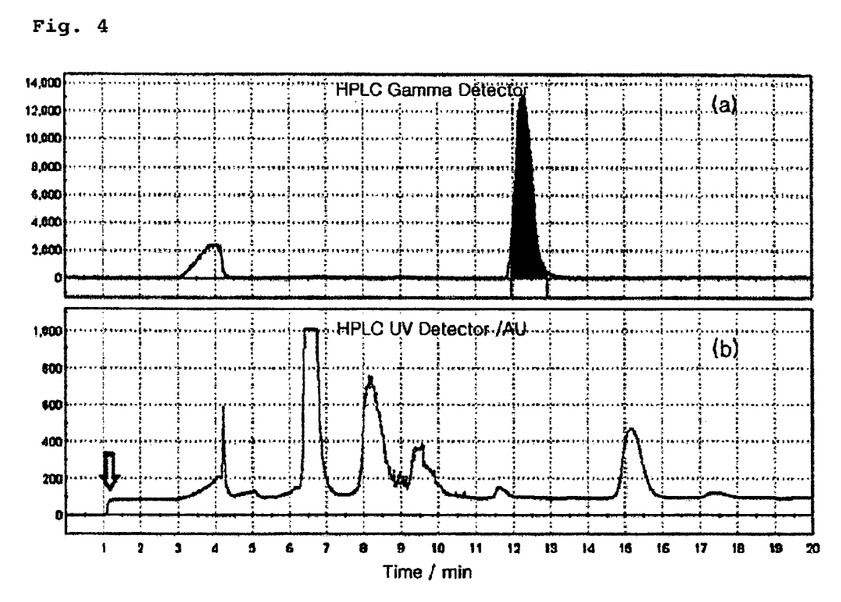
FIG. 4 is a HPLC profile of [$^{18}$F]fallypride according to an embodiment of the present invention, in which an upper line (a) is a graph detected by a gamma ray detector, and a lower line (b) is a graph detected by a UV detector (254 nm) and In FIG. 5, (a) is a graph detected by a gamma ray detector and (b) is a graph detected by a UV detector (254 nm) under other HPLC system (Gilson Ins. U.S.A.).
Figure 5:
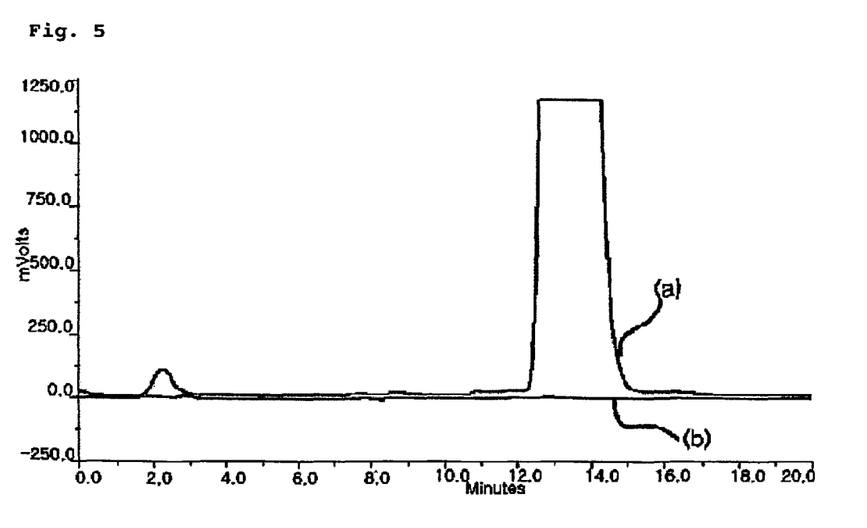

Some research groups have performed HPLC purification at 254 nm of the UV detector. Therefore, we compared UV mass patterns between 254 and 280 nm under the same radiosynthetic condition for [$^{18}$F]fallypride (entry 5). As shown in FIG. 4 the HPLC profile of UV (254 nm) showed a slight increase at 1 min which remained until the time of [$^{18}$F] fallypride separation. The total volume of the collected [$^{18}$F] fallypride was re-injected in another HPLC system (Gilson Ins. U.S.A.). However, as shown in FIG. 5, the various mass peaks were not found in the other HPLC system (UV: 254 nm).

The embodiments of the present invention will be described in details.

The following embodiments are provided only for illustrative purposes, and the contents of the present invention are not limited to the disclosed embodiments of the present invention.

<Embodiment> Preparation of [$^{18}$F]fallypride

All commercials reagent and solvents were directly used without further purifications unless otherwise specified. The reagents and solvents were purchased from Sigma-Alrich (U.S.A).

Tosylate-fallypride, (S)-N-[(1-allyl-2-pyrrolidinyl)methyl]-5-(3-toluenesulfonyloxypropyl)-2,3-dimethoxybenzamide, which was a precursor for [$^{18}$F]fallypride, and a standard [$^{18}$F]fallypride were purchased from Futurechem (Seoul, Korea). H$_2$$^{18}$O was purchased from Taiyo Nippon Sanso Corporation. [$^{18}$F]Fallypride was prepared in Seoul National University Bundang Hospital. Chromafix PS-HCO$_3$ cartridge was purchased from Macherey-Nagel Ins., (Germany, Cat. No.: 731876). tC18 Sep-Pak cartridge was purchased from Waters Corp. (U.S., Part No: WAT036810).

All radioactivity activities of each step were measured by VDC-500 from Veenstra Instruments (Netherlands) and all radiochemical yields were decay-corrected values unless otherwise noted.

Figure 1:
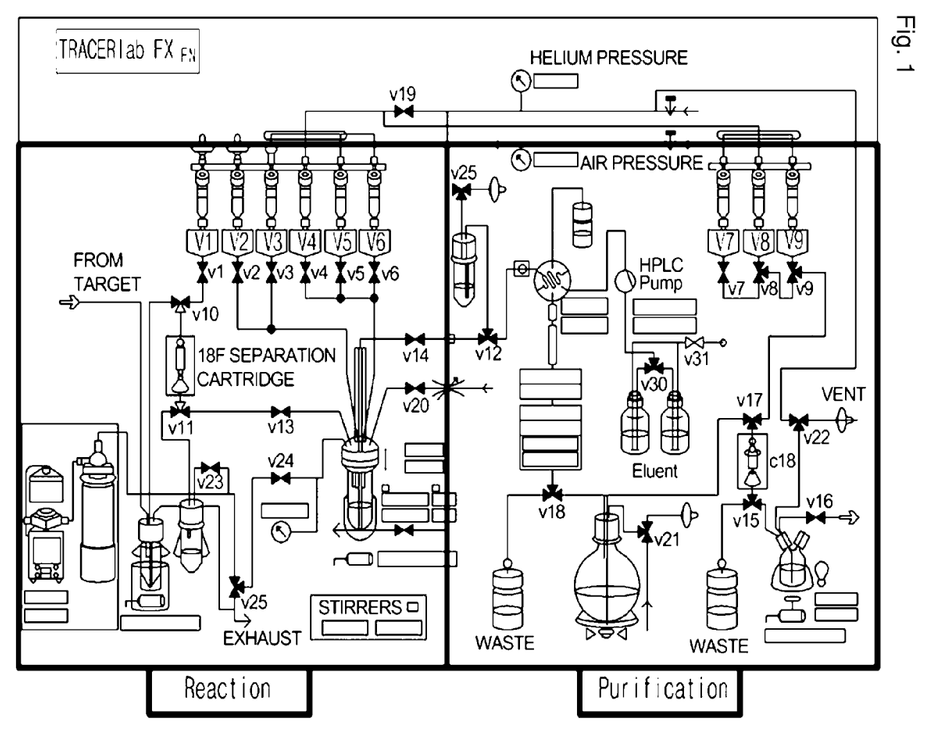
FIG. 1 is a view illustrating a construction of a TracerLab FX-FN chemical module (GE Healthcare) for a preparation of [$^{18}$F]fallypride according to an embodiment of the present invention

In details, [$^{18}$F]fallypride was prepared by TracerLab FX-FN chemical module (GE Healthcare) of FIG. 1.

First, [$^{18}$F]fluoride (8.1-26 GBq in H$_2$$^{18}$O) from target was directly delivered to fluorine-18 reservoir and transferred to Chromafix PS-HCO$_3$ cartridge during 160 sec for trapping (Step 1). The trapped fluorine-18 and TBAHCO$_3$ (10 µL) in MeOH/H$_2$O (1.0/0.2 mL) from vial 1 were moved to the carbon reaction vessel (Step 2). After complete drying for 315 sec at 65-95° C. by vacuum and He gas flow, the tosylate precursor (2 mg) in CH$_3$CN (1 mL) from vial 3 was added to the reactor and incubated at 100° C. for 10 min (Step 3). After cooling to 40° C. by air flow, the HPLC solvent from vial 5 (1.5 mL) was added to the reactor to dilute the reaction mixture, which in turn was transferred to the HPLC injector vial, after which the reactor was rinsed again with the HPLC solvent from vial 6 (1.5 mL). The combined solution in the HPLC injector vial was automatically injected into the HPLC system for thereby collecting a pure [$^{18}$F]fallypride (Step 4).

The purification of HPLC was performed in 70% CH$_3$CN/H$_2$O contained 0.6% TEA, 7 mL/min of flow rate, UV detector (280 nm) and gamma ray detector in the FX$_{FN}$ module. The collected [$^{18}$F]fallypride fraction around 12.5-13.5 min from HPLC was transferred to the vial 10 filled 100 mL of H$_2$O. The diluted solution was moved to a tC18 Sep-Pak cartridge to trap [$^{18}$F]fallypride only and to remove the HPLC solvent. The cartridge was rinsed with 10 mL of H$_2$O from vial 9 and then collected by 1 mL of EtOH from vial 8. Finally, 10 mL of saline from vial 7 was eluted to the sterile vial for adjustment of 10% ethanol/saline. Consequently, [$^{18}$F]fallypride was obtained with high radiochemical yield about 68±1.6% (decay-corrected, n=11), and the total preparation time was 51±1.2 minutes.

<Analysis>

The prepared [$^{18}$F]fallypride was detected by a gamma ray and a UV detector in order to confirm the production of [$^{18}$F]fallypride, and it was shown on a HPLC chromatography. A result of the detection is shown in FIG. 2.

Figure 2:
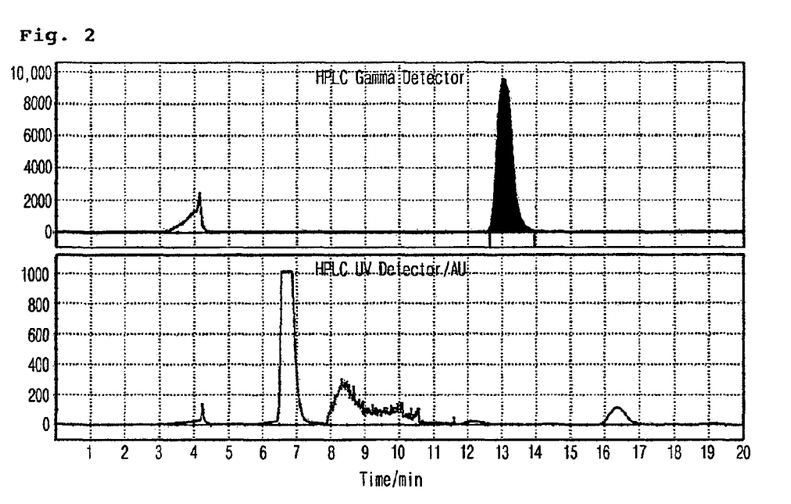
FIG. 2 is a HPLC profile of [$^{18}$F]fallypride according to an embodiment of the present invention, in which an upper part (a) is a gamma ray detector profile, and a lower part (b) is a UV (280 nm)

As shown in FIG. 2, an upper line is a graph detected by a gamma ray detector, and a lower line is a graph detected by a UV detector (280 nm).

As shown in FIG. 2, a larger peak was observed in the graph detected by a gamma ray; no peak was observed in the graph detected by UV in the same position, with a result of which it is possible to confirm that the prepared substance has a high purity.

The prepared [$^{18}$F]fallypride was confirmed by HPLC after re-injection with a non-radioactivity substance ([$^{19}$F]fallypride) while having the same chemical structure. The detections of [$^{18}$F]fallypride was performed by a gamma ray and a UV detector (280 nm), and a result of the detection was shown in a HPLC chromatography as shown in FIG. 3.

Figure 3:
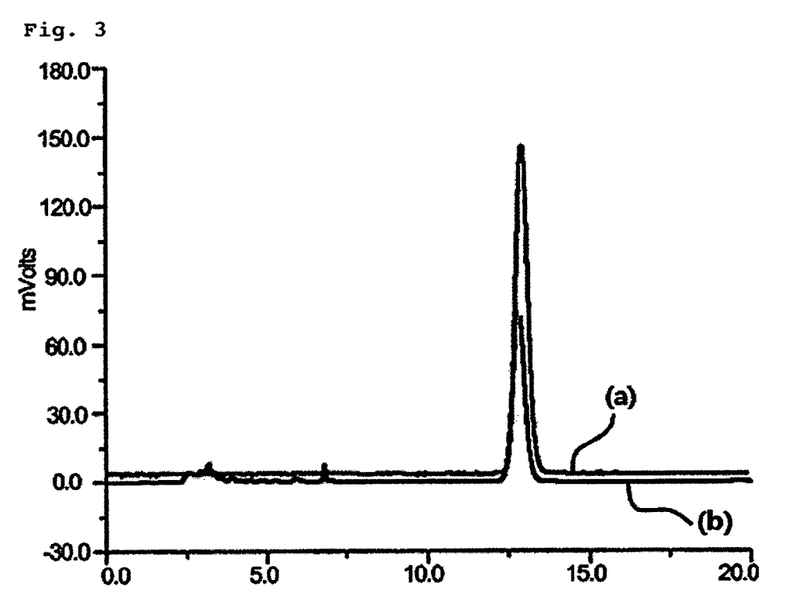
FIG. 3 is a HPLC co-injected profile of a [$^{18}$F]fallypride prepared according to an embodiment of the present invention with a standard [$^{18}$F]Fallypride ($^{19}$F), in which (a) is a gamma ray, and (b) is a UV (280 nm)

As shown in FIG. 3, (a) is a graph detected by a gamma ray detector and (b) is a graph detected by a UV detector (280 nm).

As shown in FIG. 3, it was known that the peak detected by a UV and the peak detected by a gamma ray were on the same positions, with a result of which it is possible to confirm that the substance prepared by the present invention is [$^{18}$F]fallypride.

As shown in FIG. 4, an upper line is a graph detected by a gamma ray detector, and a lower line is a graph detected by a UV detector (254 nm).

As shown in FIG. 4, a larger peak was observed in the graph detected by a gamma ray; no peak also was observed in the graph detected by 254 nm of UV in the same position, with a result of which it is possible to confirm that the prepared substance has a high purity.

As shown in FIG. 5, (a) is a graph detected by a gamma ray detector and (b) is a graph detected by a UV detector (254 nm) under other HPLC system (Gilson Ins. U.S.A.)

As shown in FIG. 5, it was known that the peak detected by a UV (254 nm) and no peak also was observed in the graph detected by 254 nm of UV, with a result of which it is possible to confirm that [$^{18}$F]fallypride prepared by the present invention also has high purity in 254 nm of UV.

<Experiment 1> Recovery Measurement of Fluorine-18

The separation of Fluorine-18 from Chromafix PS-HCO$_3$ is performed after radioactive fluorine-18 in H$_2$$^{18}$O water is collected in Chromafix PS-HCO$_3$, and the fluorine-18 is isolated and recovered by means of a phase-transfer catalyst (base) and elution solvent.

The amount of recovered fluorine-18 is based on a reactive substance in the course of preparing [$^{18}$F]fallypride according to the present invention while influencing the synthetic yield of [$^{18}$F]fallypride. So, it is needed to measure the recovery ratio of fluorine-18 as follows in order to known the optimum combination of the phase-transfer catalyst (base) and the elution solvent.

*In more details, K2.2.2./$K_2CO_3$ or 40% $TBAHCO_3$ were used as the phase-transfer catalyst (base), and $CH_3CN/H_2O$ or $MeOH/H_2O$ was used as elution solvent. The recovery ratio of the fluorine-18 at Chromafix PS-$HCO_3$ was measured while changing the concentration of the phase-transfer catalyst (base), a result of which was shown in Table 1.

TABLE 1

| Classification | Phase-transfer catalyst (base) | Solvent (1.0/0.2 mL) | Recovery ratio of fluorine-18 (%) |
|---|---|---|---|
| 1 | K2.2.2./$K_2CO_3$ (5.5/0.5 mg) | $CH_3CN/H_2O$ | ~18 |
| 2 | K2.2.2./$K_2CO_3$ (5.5/1.5 mg) | $CH_3CN/H_2O$ | ~57 |
| 3 | K2.2.2./$K_2CO_3$ (13/3.0 mg) | $CH_3CN/H_2O$ | >95 |
| 4 | K2.2.2./$K_2CO_3$ (11/0.5 mg) | $MeOH/H_2O$ | ~88 |
| 5 | K2.2.2./$K_2CO_3$ (11/0.8 mg) | $MeOH/H_2O$ | >95 |
| 6 | 40% $TBAHCO_3$ (10 μL) | $CH_3CN/H_2O$ | ~52 |
| 7 | 40% $TBAHCO_3$ (20 μL) | $CH_3CN/H_2O$ | ~74 |
| 8 | 40% $TBAHCO_3$ (30 μL) | $CH_3CN/H_2O$ | >95 |
| 9 | 40% $TBAHCO_3$ (5 μL) | $MeOH/H_2O$ | ~80 |
| 10 | 40% $TBAHCO_3$ (10 μL) | $MeOH/H_2O$ | >95 |

As seen in Table 1, when the phase-transfer catalyst (base) was K2.2.2./$K_2CO_3$ (13/3.0 mg) in $CH_3CN/H_2O$, the phase-transfer catalyst (base) was K2.2.2./$K_2CO_3$ (11/0.8 mg) in $MeOH/H_2O$, the phase-transfer catalyst (base) was 40% $TBAHCO_3$ (30 μL) in $CH_3CN/H_2O$, and the phase-transfer catalyst (base) was 40% $TBAHCO_3$ (10 μL) in $MeOH/H_2O$, the recovery ratios of fluorine-18 were above 95%, respectively. Consequently, when $MeOH/H_2O$ solution was used, trapped F-18 could be extracted with relatively low base concentration (phase-transfer catalyst) over 95% from ion cartridge more than that of $CH_3CN/H_2O$ solution.

<Experiment 2> Radiochemical Yield and Total Preparation Time Measurement

In the method for preparing [$^{18}$F]fallypride according to the present invention, the following experiments were performed in order to determine what the phase-transfer catalyst (base) and the elution solvent influence the radiochemical yield and total preparation time of [$^{18}$F]fallypride.

The [$^{18}$F]fallypride was prepared in the same method as the embodiment with the reaction time of being 30 minutes and 10 minutes, respectively, by using a combination of four phase-transfer catalysts (base) and solvents which had the best recovery ratio of fluorine-18 as a result of the experiment 1, and the radiochemical yield and total preparation time of the [$^{18}$F]fallypride were measured, the results of which are shown in Table 2.

TABLE 2

| Classification | Phase-transfer catalyst (base) | Solvent (1.0/0.2 mL) | Reaction time (minutes) | Radio-chemical yield (%) | Total preparation time (minutes) |
|---|---|---|---|---|---|
| 1 | K2.2.2./$K_2CO_3$ (13/3.0 mg) | $CH_3CN/H_2O$ | 30 | 26 ± 4.9 | 74 ± 1.2 |
| 2 | K2.2.2./$K_2CO_3$ (11/0.8 mg) | $MeOH/H_2O$ | 30 | 71 ± 1.9 | 74 ± 1.2 |
| 3 | 40% $TBAHCO_3$ (30 μL) | $CH_3CN/H_2O$ | 30 | 44 ± 4.1 | 74 ± 1.2 |
| 4 | 40% $TBAHCO_3$ (10 μL) | $MeOH/H_2O$ | 30 | 71 ± 1.2 | 74 ± 1.2 |
| 5 | 40% $TBAHCO_3$ (10 μL) | $MeOH/H_2O$ | 10 | 68 ± 1.6 | 51 ± 1.2 |

As seen in Table 2, When the phase-transfer catalyst (base) was 40% $TBAHCO_3$ (10 μL) in $MeOH/H_2O$ (entry 4), the radiochemical yield of [$^{18}$F]fallypride was higher 71% as compared to the other experiment, and the specific activity was 140-192 GBq/μmol. When the phase-transfer catalyst (base) was K2.2.2./$K_2CO_3$ (11/0.8 mg) in $MeOH/H_2O$ (entry 2), the yield was 71%, but the unknown side products with [$^{18}$F]fallypride was slightly erupted at the same time, which resulted in a lower specific activity.

In event of the reaction time, when the phase-transfer catalyst (base) was 40% $TBAHCO_3$ (10 μL) in $MeOH/H_2O$, the radiochemical yield of the prepared [$^{18}$F]fallypride was 71% (entry 4), and when the reaction time was 10 minutes under same condition, the radiochemical yield of the prepared [$^{18}$F]fallypride was 68%. At this moment, although a slightly better radiochemical yield seemed to be obtained when the reaction time was 30 minutes, the radiochemical yield value of Table 2 was the value decay-corrected. As the values which were not decay-corrected, the above two events showed 46~49% of radiochemical yields which were similar with each other.

Therefore, it was known that when the phase-transfer catalyst (base) was 40% $TBAHCO_3$ (10 μL) in $MeOH/H_2O$ and the reaction time was 10 minutes, it was possible to obtain a higher radiochemical yield. The total preparation time was shorter than other condition about 20 minutes. The above condition was the best for preparing [$^{18}$F]fallypride. In addition, the present invention proceeds at relatively lower temperature (100° C.) than reported conditions (150-165° C.) as use of low base concentration method and no use an unusual microwave system in automatic devices.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. An automated method for preparing (S)-N-[(1-allyl-2-pyrrolidinyl)methyl]-5-(3-[$^{18}$F]-fluoropropyl)-2,3-dimethoxybenzamide ([$^{18}$F]fallypride), comprising:
 absorbing a fluorine-18 to a polymer ion exchange cartridge;
 extracting fluorine-18 by inputting 5.0-25 μL of 40% $TBAHCO_3$ or 4,7,13,16,21,24-hexaoxa-1,10-diazabicyclo[8.8.8]hexacosane (K2.2.2)/$K_2CO_3$ (5-25 mg/0.5-3.0 mg) as a phase-transfer catalyst in a mixture of alcohol/water (1.0/0.2 (v/v)) or alcohol as an elution solvent into the polymer ion exchange cartridge trapped by the fluorine-18;
 preparing a (S)-N-[(1-allyl-2-pyrrolidinyl)methyl]-5-(3-[$^{18}$F]-fluoropropyl)-2,3-dimethoxybenzamide ([$^{18}$F]fallypride) product by removing the solvent from the extracted fluorine-18, by inputting tosylate precursor in CH₃CN as a reaction solvent into a reactor and by reacting the same 5-35 minutes at 50-120° C.; and purifying a pure (S)-N-[(1-allyl-2-pyrrolidinyl)methyl]-5-(3-[$^{18}$F]-fluoropropyl)-2,3-dimethoxybenzamide ([$^{18}$F]fallypride) by separating the prepared (S)-N-[(1-allyl-2-pyrrolidinyl)methyl]-5-(3-[$^{18}$F]-fluoropropyl)-2,3-dimethoxybenzamide ([$^{18}$F]fallypride) product.

2. The method of claim 1, wherein the polymer ion exchange cartridge is either a quaternary methylammonium (QMA) cartridge or a polystyrene-bicarbonate (PS-HCO₃) cartridge.

3. The method of claim 1, wherein the alcohol has a straight-chained or branch-chained alkyl group having from 1 to 6 carbon atoms.

4. The method of claim 1, wherein the (S)-N-[(1-allyl-2-pyrrolidinyl)methyl]-5-(3-[$^{18}$F]-fluoropropyl)-2,3-dimethoxybenzamide ([$^{18}$F]fallypride) has 65-75% of a radiochemical yield.

5. The method of claim 1, wherein the total preparation time is 40-45 minutes.

6. The method of claim 1, wherein the preparation method is applied to a preparation of either N-2-fluoropropyl-3-β-(4-iodophenyl)nortropane-2-β-carboxylic acid (FP-CIT), 1-(5-Deoxy-5-fluoro-α-D-arabinofuranosyl)-2-nitroimidazole (FAZA) or 2-(1,1-Dicyanopropen-2-yl)-6-(fluoroethyl)methylamino)naphthalene (FDDNP), all of which are sensitive to a base.

* * * * *